United States Patent  (10) Patent No.: US 9,051,182 B2
Kalb  (45) Date of Patent: Jun. 9, 2015

(54) METHOD OF USE OF AN IONIC LIQUID FOR STORING HYDROGEN

(75) Inventor: Roland Kalb, Loeben (AT)

(73) Assignee: VTU HOLDING GMBH, Grambach (AT)

( * ) Notice: Subject to any disclaimer, the term of this patent is extended or adjusted under 35 U.S.C. 154(b) by 653 days.

(21) Appl. No.: 13/144,912

(22) PCT Filed: Jan. 8, 2010

(86) PCT No.: PCT/EP2010/000062
§ 371 (c)(1),
(2), (4) Date: Oct. 18, 2011

(87) PCT Pub. No.: WO2010/081657
PCT Pub. Date: Jul. 22, 2010

(65) Prior Publication Data
US 2012/0027669 A1     Feb. 2, 2012

(30) Foreign Application Priority Data

Jan. 15, 2009 (EP) .................................. 09150676

(51) Int. Cl.
  *C01B 6/23*   (2006.01)
  *C01B 3/06*   (2006.01)
  *C01B 3/00*   (2006.01)
  *C07C 211/63* (2006.01)
  *C07F 9/54*   (2006.01)

(52) U.S. Cl.
  CPC . *C01B 3/065* (2013.01); *C01B 6/23* (2013.01); *C01B 3/001* (2013.01); *C07C 211/63* (2013.01); *C07F 9/5407* (2013.01); *Y02E 60/327* (2013.01); *Y02E 60/362* (2013.01)

(58) Field of Classification Search
  USPC ........................ 423/648.1, 652, 657
  See application file for complete search history.

(56) References Cited

U.S. PATENT DOCUMENTS

| 3,166,514 A * | 1/1965 | Parshall .................... 252/188.25 |
| 6,866,689 B2 * | 3/2005 | Lumsden et al. ............... 44/300 |
| 2001/0053472 A1 | 12/2001 | Edlund |
| 2006/0060817 A1 | 3/2006 | Tempel et al. |
| 2006/0102489 A1 | 5/2006 | Kelly |
| 2009/0081118 A1 | 3/2009 | Gerhard et al. |

FOREIGN PATENT DOCUMENTS

DE     102007039478 A1    2/2009

(Continued)

OTHER PUBLICATIONS

Douglas et al. "Preparation of Quaternary Ammonium Borohydrides from Sodium and Lithium Borohydrides", 1951, vol. 74 p. 2346-2348.*

Amir Doroodian, et al.; Methylguanidinium Borohydride: An Ionic-Liquid-Based Hydrogen-Storage Material; Angewandte Chronical; DOI:10.1002/anie.200905359; pp. 1871-1873.

(Continued)

*Primary Examiner* — Stanley Silverman
*Assistant Examiner* — Syed Iqbal
(74) *Attorney, Agent, or Firm* — Knobbe Martens Olson & Bear LLP

(57) ABSTRACT

A method of storing hydrogen is provided, wherein the method comprises forming a first ionic liquid by inducing a borohydride into a second ionic liquid comprising cations and an anion comprising borate, in particular metaborate, and forming the second ionic liquid by releasing the hydrogen out of the first ionic liquid by using water and/or a catalyst.

18 Claims, 2 Drawing Sheets

(56) References Cited

FOREIGN PATENT DOCUMENTS

| | | | |
|---|---|---|---|
| DE | 102008013617 | A1 | 9/2009 |
| WO | 2006103812 | A1 | 10/2006 |
| WO | 2009095012 | A1 | 8/2009 |
| WO | 2009101201 | A2 | 8/2009 |

OTHER PUBLICATIONS

Marcelo P. Stracke, et al.; Hydrogen-Storage Materials Based on Imidazolium Ionic Liquids; Energy & Fuels 2007, 21, pp. 1695-1698.
C:\EPOPROGS/SEA\.\..\..\epodata\sea\eplogf\interla.log; Jul. 6, 2010 09:11:43; pp. 1-5.

* cited by examiner

METHOD OF USE OF AN IONIC LIQUID FOR STORING HYDROGEN

CROSS-REFERENCE TO RELATED APPLICATIONS

This application is the U.S. National Phase under 35. U.S.C. §371 of International Application PCT/EP2010/000062, filed Jan. 8, 2010, which claims priority to European Patent Application No. 09150676.6, filed Jan. 15, 2009. The International Application was published under PCT Article 21(2) in English.

FIELD OF THE INVENTION

The invention relates to a method of use of an ionic liquid for storing hydrogen.

Further, the invention relates to an ionic liquid for storing hydrogen.

BACKGROUND OF THE INVENTION

The storage and distribution of hydrogen can be effected in different ways. For example, hydrogen can be stored in compressed form in suitable high-pressure tanks which allow storage at up to a pressure of 875 bar. Further, storage of the liquefied low-temperature hydrogen in suitable cryogenic containers, preferably in superinsulated cryogenic containers is known. The last named possibility is implemented in particular with hydrogen-powered vehicles-independently of whether they are powered by means of a modified combustion engine or by means of a fuel cell which drives an electric motor.

Storage systems are in the experimental stage in which the storage of the hydrogen takes place in organic compounds capable of hydrogenation which are able to chemically bind the hydrogen. Such storage systems are known under the designations MPH (methylcyclohexane poluene hydrogen), decaline/napthalene and n-heptane/toluene system.

Common to the aforementioned systems is that the hydrogen is brought to reaction with them under suitable conditions so that hydrogenation and storage of the hydrogen results.

All the aforementioned alternatives have specific advantages and disadvantages so that the decision in favor of one of the alternatives is usually determined by the specific applications and circumstances. The fundamental disadvantage of the last-named alternative until now has been that the chemical reaction systems used have relatively high vapor pressures, are thus volatile and contaminate the hydrogen to a considerable degree.

To achieve high degrees of purity for the hydrogen in particular, such reaction systems must, therefore, be removed, often at great expense in terms of technology and/or energy.

The person skilled in the art is continuously striving to create a storage potential for hydrogen which allows storage of the hydrogen in a pure or absolutely pure form, where storage should be possible in the safest and most economical manner possible. Hydrogen is needed in a very pure form particularly in the operation of fuel cells. In the case of the modified combustion engines mentioned as well, which usually have a downstream catalytic converter, storage of the hydrogen in (ultra)pure form is striven for since otherwise the hydrocarbons entrained with the hydrogen (may) have a negative effect on the activity and life of the catalytic converter. Particularly in the use of hydrogen in the so-called mobile applications-operation of vehicles, etc.—the safety aspect is paramount; this applies especially for the refueling process which is usually performed by the driver himself and therefore by a "technical layman."

Thus, there may be a need for an alternative method of storing hydrogen, which method may be efficient and/or secure.

OBJECT AND SUMMARY OF THE INVENTION

It may be an objective of the invention to provide a method for storing hydrogen and a medium for storing hydrogen which method may be efficient and/or may provide a secure method of operation.

This object may be solved by a method of use of an ionic liquid for storing hydrogen and an ionic liquid for storing hydrogen according to the independent claims. Further exemplary embodiments are described in the dependent claims.

According to an exemplary aspect of the invention a method of storing hydrogen is provided, wherein the method comprises forming a first ionic liquid by inducing a borohydride into a second ionic liquid comprising cations and an anion comprising borate, in particular metaborate, and forming the second ionic liquid by releasing the hydrogen out of the first ionic liquid by using water and/or a catalyst. That is, a loop process or cycle process may be formed in which an ionic liquid is used to store hydrogen, e.g. in the form of a borohydride, wherein the ionic liquid or more specifically the anion of the same is changed from a first one, e.g. borohydride, to a second one, e.g. metaborate or borate or polyborate. In such a process the hydrogen may be stored in the form of a specific anion of an ionic liquid, e.g. borohydride, and is then released whereby a second anion is formed, e.g. a metaborate or borate or polyborate, resulting in a second ionic liquid which may then be loaded again with hydrogen. In particular, the borohydride may be sodium borohydride ($NaBH_4$). In particular, a fluid of borohydride ionic liquid and water may be transformed into an emulsion before a catalyst is introduced. Thus, a surface of the phase interface may be increased. In particular, the emulsion may be generated without an emulsifier, e.g. by whirling the fluid or by causing the fluid to flow against a deflector or baffle plate. The save of an emulsifier may simplify a subsequent recycling of the borohydride.

In particular, the borohydride may form an anion of the first ionic liquid. The first and/or the second ionic liquid may be a pure ionic liquid, i.e. a liquid substantially only containing anions and cations, while not containing other components, e.g. water. Alternatively a solution containing the ionic liquid and a solvent or further compound may be used, e.g. in order to decrease viscosity. For clarity reasons it should be mentioned that the ionic liquid may of course comprise a plurality of cations and anions. The ionic liquid may be an organic salt having a relatively low melting point, e.g. a melting point which is below 100° C. That is, a material may be specified as an ionic liquid although it is solid at room temperature or has at least a high viscosity at room temperature.

In particular, the cation may be a hydrophobic cation, which term may particularly denote an ionic liquid having a strong miscibility gap with respect to water in a temperature range between 0° C. and 60° C., more particularly, in the range between 0° C. and 80° C. and preferably in the range between 0° C. and 100° C.

According to an exemplary aspect of the invention an ionic liquid for storing hydrogen is provided, wherein the ionic liquid comprises a cation and borohydride. In particular, the borohydride may be part of or may form the anion of the ionic liquid. The cation may comprise or may consist of quaternary materials, e.g. trioctylmethylammonium or 1-octyl-3-methyl-imidazolium. Furthermore, the ionic liquid may have a predetermined viscosity value. In particular, the viscosity value may be set, e.g. according to a desired level, e.g. below 100 mPas at room temperature and/or below 2000 mPas at −20° C.

According to an exemplary aspect of the invention an ionic liquid for storing hydrogen is provided, wherein the ionic liquid comprises a cation and an anion comprising borate, in particular metaborate. The borate may comprise or may consist of B, O and in some cases H-Atoms and may be formed by metaborate or polyborate. In particular, the borate or metaborate may be part of or may form the anion of the ionic liquid. The cation may comprise or may consist of quaternary material, e.g. trioctylmethylammonium. Furthermore, the ionic liquid may have a predetermined viscosity value. In particular, the viscosity value may be set, e.g. according to a desired level.

In this application the term "borohydride" may be used in the broadest possible way, i.e. may particularly denote any molecule, compound, radical or complex which comprises boron and at least one hydrogen atom. That is, every compound which can be written by the generic formula BHR'R"R''' or $BH_3X^-$ or $B_2H_6X^-$, where $X^-$ is any anion forming complexes with borane or diborane, may be denoted as borohydride. For example, R', R", R''' may be hydrogen atoms, C1-C20-alkyl, alkenyl, alkinyl, cycloalkyl, cycloalkenyl, aryl or heteroaryl, wherein each rest R may be independently substituted by one of the moiety stated above.

By providing a borohydride ionic liquid, e.g. the first ionic liquid, it may be possible to provide a method of storing hydrogen and an ionic liquid for storing hydrogen which method may be efficient and/or may provide a secure method of operation. In particular, the borohydride may form together with the cation an ionic liquid enabling an easy and secure handling which may be used as an energy source or energy carrier for cars, for example. In particular, the handling may be similar to common gasoline, since the ionic liquid may also be a liquid as common gasoline. Thus, no pressurized hydrogen or additional carriers like metal hydrides may be necessary, which may only be formed under specific conditions. Therefore, the use of ionic liquids may be more secure since no specific conditions may be necessary or at least the restrictions concerning specific conditions, e.g. temperature range, may be lessened. It should be noted that the viscosity of the ionic liquid may be decreased by adequate provisions, e.g. by increasing the temperature. The use of such ionic liquids for hydrogen storage may also provide a storing medium which may induce low corrosion in containers or the like used to store the ionic liquid. Thus, it may be possible to omit a corrosion inhibitor.

Next, further aspects of exemplary embodiments of the method of an ionic liquid for hydrogen storing are described. However, these embodiments also apply for the ionic liquid for storing hydrogen comprising borate or borohydride.

According to an exemplary embodiment of the method the cation is a quaternary or protonated cation.

According to an exemplary embodiment of the method the cation comprises one to four moieties out of the group consisting of hydrogen, C1-C20-alkyl, C1-C20-alkenyl, C1-C20-alkinyl, C1-C20-cycloalkyl, C1-C20-cycloalkenyl, C1-C20-aryl, and C1-C20-heteroaryl.

Preferably, the one to four, i.e. one, two, three or four, moieties may be selected out of the group consisting of hydrogen, C1-C10-alkyl, C1-C10-alkenyl, C1-C10-alkinyl, C1-C10-cycloalkyl, C1-C10-cycloalkenyl, C1-C10-aryl, and C1-C10-heteroaryl. More preferably the one to four moieties may be selected out of the group consisting of hydrogen, C1-C8-alkyl, C1-C8-alkenyl, C1-C8-alkinyl, C1-C8-cycloalkyl, C1-C8-cycloalkenyl, C1-C8-aryl, and C1-C8-heteroaryl.

For clarity reasons it should be mentioned that in this application the term C1-C20-alkyl or similar terms is an abbreviatory notation for C1-alkyl, C2-alkyl, . . . , up to C20-alkyl or similar terms.

According to an exemplary embodiment of the method the cation is one out of the group consisting of pyridinium, pyrrolium, thiazolium, oxazolium, and quinolinium, wherein one moiety is bound to the nitrogen atom and/or one to three moieties are bound to carbon atoms of the carbon ring.

According to an exemplary embodiment of the method the cation is one out of the group consisting of ammonium, phosphonium, and sulfonium.

According to an exemplary embodiment of the method the cation is one out of the group consisting of piperidinium, pyrrolidinium and morpholinium, wherein one or two of the one to four moieties is bound to the nitrogen atom and/or one to three of the one to four moieties are bound to carbon atoms of the carbon ring.

According to an exemplary embodiment of the method the cation is one out of the group consisting of imidazolium, benzimidazolium, pyrazolium, and benzotriazolium, wherein a respective one of the one to four moieties is bound to each nitrogen atom and/or one to three of the one to four moieties are bound to carbon atoms of the carbon ring. For clarity reasons it should be noted that in case of more than one nitrogen atom a first moiety may be bound to a first nitrogen atom and a second moiety may be bound to a second nitrogen atom.

According to an exemplary embodiment of the method the cation is one out of the group consisting of trioctylmethylammonium, trihexylmethylammonium, tetrahexylammonium, tetraoctylammonium, and 1-octyl-3-methylimidazolium. In particular, trioctylmethylammonium may form the cation of the ionic liquid.

In particular, the cation may be free of an alkaline metal and/or an alkaline earth metal. That is, ionic liquid may not comprise a alkaline metal cation and/or an alkaline earth metal cation.

According to an exemplary embodiment of the method the catalyst is a transition metal and/or a noble metal. In particular, the noble metal may be platinum, palladium, rhodium or the like and the transition metal may be cobalt, nickel, copper or lanthanides or the like. Furthermore, it should be noted that the catalyst may be formed by an alloy, intermetallic compound, chemical compound, complex, or ceramic consisting of or comprising one of the above mentioned noble metals and/or transition metals. Additionally, the catalyst may be immobilized, chemically and/or physically, on or in a medium, e.g. activated charcoal, ceramics, zeolite, nano tubes, fullerene, plastics, membranes or the like.

According to an exemplary embodiment of the method the catalyst forms a microcrystalline or nanocrystalline structure.

The term "microcrystalline structure" may particularly denote a crystallized structure having elements which have a size in the order of micrometers. In an analogous definition the term "nanocrystalline structure" may particularly denote a crystallized structure having elements which have a size in the order of nanometers. For example, the catalyst structure may be formed by sintering metal powder having particle sizes in the range of micrometers and nanometers, respectively, e.g. 0.2 micrometer to 1.6 micrometer or about 10 nanometers. These powder particles may be sintered to spheres having a diameter in the range of millimeter, e.g.

between 0.1 mm and 20 mm, particularly between 1 mm and 2 mm. After sintering the spheres the same may be sintered to form a crystal like structure, e.g. to form a hexagonal sphere packing in particular a densest hexagonal sphere packing or highest density hexagonal sphere packing. Such structures may be particularly useful to provide a great surface so that a reaction may be enabled, e.g. the releasing of the hydrogen may be promoted. In particular, the densest sphere packing may force a viscous ionic liquid to contact the whole surface of the catalyst.

According to an exemplary embodiment of the method by the releasing of the hydrogen a borate, e.g. metaborate or any compound corresponding to the generic formula BOR or BORR', is formed.

In particular, the metaborate may form the anion of an ionic liquid.

According to an exemplary embodiment of the method the first ionic liquid and/or the second ionic liquid has a predetermined viscosity value. In particular, the first ionic liquid and the second ionic liquid may have the same viscosity or different viscosity. For example, a first predetermined viscosity value may be associated with the first ionic liquid, while a second predetermined viscosity level may be associated with the second ionic liquid. In particular, the viscosity value may be set, e.g. according to a desired level, e.g. below 100 mPas at room temperature and/or below 2000 mPas at −20° C.

According to an exemplary embodiment the viscosity level is set to the predetermined viscosity value by adding an additive. In particular, the additive may be adapted to decrease the viscosity, e.g. may be an agent having a lower viscosity than the ionic liquid, i.e. the hydrogen storing liquid. Furthermore, the additive may not react with the ionic liquid and/or a used catalyst. Thus, in general no esters, aldehydes, ketones, carbonic acids may be used beside ones which are sterically inhibited, i.e. aldehydes, ketones or carbonic acids which does not react with the ionic liquid and/or catalyst due to sterically inhibiting may be used for example.

In general, additives may be protective additives, e.g. for protection for corrosion, wear, high pressure, oxidation and/or reduction processes, buffering substances, e.g. for ph level buffering and/or acid capturing agents, complexing agents, emulgators, dispersion mediums, detergents, lubricants, friction modification agents, viscosity modification agents, gelling agents, sealing agents, preservative agents, so-called pour-point additives, foam inhibitors, radical interceptors, and water regulating agents.

In particular, an additive may be used having a low vapor pressure, high boiling point and a low freezing point. Additionally, an additive may be used which can be readily removed out of hydrogen gas, e.g. as a gas phase. The removing may be effected by an adsorbent, e.g. activated charcoal. Furthermore, the used additive may not be solvable in or mixable with water so that it may not be removed during a recycling process.

According to an exemplary embodiment the additive is one out of the group consisting of amide, ether, including cyclic or polyether, acetals, ketals, alcohols, including polyalcohols, aromatic hydrocarbons, aliphatic hydrocarbons, e.g. butanols, pentanols, hexanols, heptanols, octanols, fatty alcohols, dibutylethers, diethylethers, methyl tert-butyl ethers, ethyl tert-butylethers, 1,2-diethoxyethanes, formaldehyde dimethylacetales, polyethylene glycol dimethylethers of different chain lengths, and polyvinyl alcohols of different chain lengths.

According to an exemplary embodiment the method further comprises adding a basic additive to the first ionic liquid and/or the second ionic liquid. That is, an additive may be used having a pH-value of more than 7. In particular, the basic additive may have a stabilizing effect and may also be called stabilizer.

According to an exemplary embodiment of the method the basic additive is at least one out of the group consisting of alkaline metal hydroxides, alkaline earth metal hydroxides, alkaline metal carbonates, alkaline earth metal carbonates, quaternary tetraalkylammonium hydroxides, quaternary tetraalkylammonium carbonates, quaternary tetraalkylphosphonium hydroxides, quaternary tetraalkylphosphonium carbonates, and alkylcarbonates. In particular, a mixture of more than one of the mentioned basic additives may be used.

Summarizing, according to an exemplary aspect of the invention a process for storing hydrogen may be provided. The process may form a closed loop and may be based on liquid carrier materials, like ionic liquids. In particular, the liquid carrier may comprise cations, e.g. trioctylmethylammonium, and anions which may be formed by borohydride and which may carry the stored hydrogen. The cations and anions may form an ionic liquid which may stable even when in contact with water. However, the stored hydrogen may be released by using water and a respective catalyst, e.g. a transition metal or noble metal like platinum, palladium or rhodium. Under these circumstances the ionic liquid may release the hydrogen while a new ionic liquid may be formed comprising trioctylmethylammonium and a borate, e.g. metaborate. This new ionic liquid may then be loaded with hydrogen again, e.g. by introducing sodium borohydride into the ionic liquid.

The respective method of storing hydrogen by using an ionic liquid may provide an efficient and secure way of storing hydrogen. In particular, it may be possible to store a sufficient amount without using high pressure or low temperatures. For example, the use of ionic liquids comprising trioctylmethylammonium as a cation and metaborate or borohydride as anions may enable the provision of liquid storage media wherein the ionic liquid may be loaded and unloaded with hydrogen in a cycle or recycling process, e.g. by using a liquid ion exchange process. This ionic liquid may provide a sufficiently high storage density of the hydrogen which may be released in a controllable manner by using a catalyst. In general it may be possible to provide a storage medium ensuring a sufficient range for a car, for example. By using an ionic liquid as storage media it may be possible to ensure a high storage capacity per mass and/or a high storage capacity per volume. Additionally, low leakage possibly leading to a high storage security may be achievable. Furthermore, the described ionic liquids may have a high stability over time with respect to chemical and/or thermal influences and/or may be flame resistant.

Other possible cations may include tetramethylammonium, tetraethylammonium, triethylmethylammonium, tetrabutylammonium, tributylmethylammonium, 1,3-dimethylimidazolium, 1-butyl-3-methylimidazolium, 1,2,3-trimethylimidazolium, 1-ethyl-3-methylimidazolium, 1-ethyl-2,3-dimethylimidazolium, and 1-butyl-2,3-dimethylimidazolium which may all be used together with $BH_4$ as an anion.

The aspects defined above and further aspects of the invention are apparent from the examples of embodiment to be described hereinafter and are explained with reference to these examples of embodiment. It should be noted that features described in connection with one exemplary embodiment or exemplary aspect may be combined with other exemplary embodiments and other exemplary aspects.

BRIEF DESCRIPTION OF THE DRAWINGS

The invention will be described in more detail hereinafter with reference to examples of embodiment but to which the invention is not limited.

DESCRIPTION OF EMBODIMENTS

Figure 1:
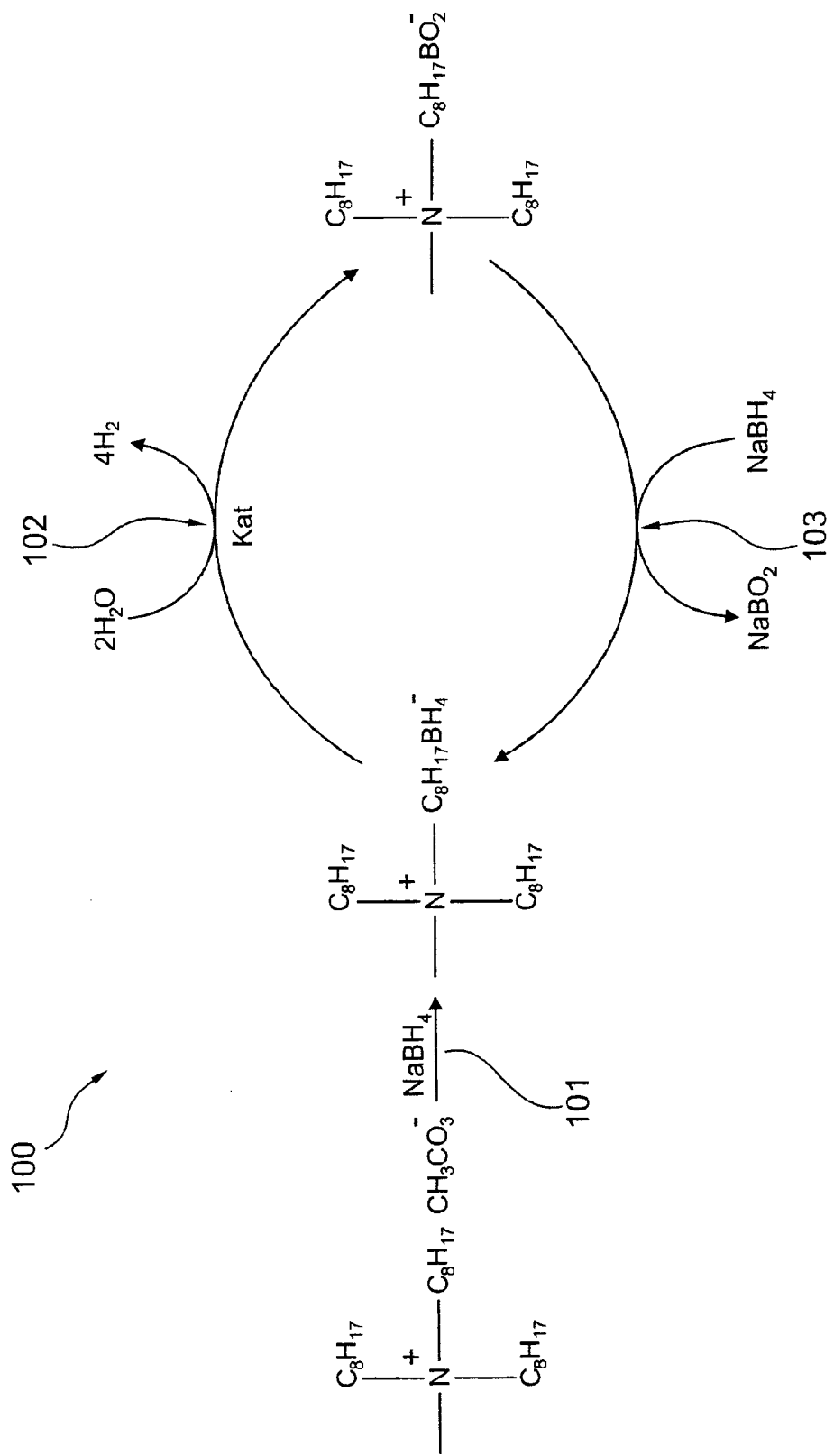
FIG. 1 schematically illustrates a cycle process for hydrogen storage based on an ionic liquid.

The illustration in the drawing is schematically.

FIG. 1 schematically shows a cycle process or a recycling process 100 for hydrogen storage, which process is based on an ionic liquid. At the beginning of the process an ionic liquid may be manufactured from trioctylmethylammoniummethylcarbonate

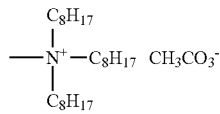

and sodium borohydride ($NaBH_4$) which is schematically depicted by arrow 101 in FIG. 1. The resulting ionic liquid is trioctylmethylammonium-borohydride (TOMA-$BH_4$)

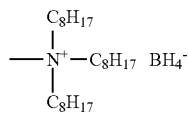

wherein trioctylmethylammonium forms the cation and the borohydride forms the anion which also includes hydrogen which may be released afterwards. TOMA-$BH_4$ is not solvable in water but may release hydrogen when brought into contact with water and a catalyst, which is schematically indicated by arrow 102.

Compared to $NaBH_4$ the use of TOMA-$BH_4$ may exhibit several advantages. For example, TOMA-$BH_4$ may be stable, while $NaBH_4$ may decompose quite fast even in alkaline environments. Furthermore, TOMA-$BH_4$ may not react with water and may not be solved in water, i.e. may form a seperate phase floating on a water phase, while $NaBH_4$ may react with water and may be solvable in water. Additionally, TOMA-$BH_4$ may exhibit a lower tendency to crystallize compared to $NaBH_4$, especially at low temperatures.

As a catalyst transition metals may be used, e.g. platinum or palladium. As a result of the releasing of hydrogen a second ionic liquid is formed which comprises trioctylmethylammonium as the cation while comprising metaborate as the anion and which can be written in the following form:

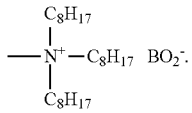

That is, trioctylmethylammonium-metaborate (TOMA-$BO_2$) is formed, which shows a significant miscibility gap with water as well. The metaborate anion may especially at elevated temperatures partially or completely react to borate or polyborate anions; anyway, this borate or polyborate anions do not disturb the process and show nearly identical properties as the metaborate anion. So the term "metaborate" herein can be seen more generally to be a mixture of metaborate and/or borate and/or polyborate. In a next step of the cycle process the TOMA-$BO_2$ may be brought into contact with aqueous solution of sodium borohydride ($NaBH_4$) which is indicated by arrow 103 leading to the formation of TOMA-$BH_4$ and an aqueous solution of sodium metaborate ($NaBO_2$) wherein TOMA-$BH_4$ and $NaBO_2$ forms two phases of the resulting liquid. These two phases can be separated leading to recycled TOMA-$BH_4$. It should be mentioned that small amounts of water in TOMA-$BH_4$ may not be of negative impact since TOMA-$BH_4$ does not react with the water in the absence of a catalyst.

The $NaBO_2$ may then be converted into $NaBH_4$ by using common methods which $NaBH_4$ may then be used again in the recycling process (arrow 103).

Figure 2:
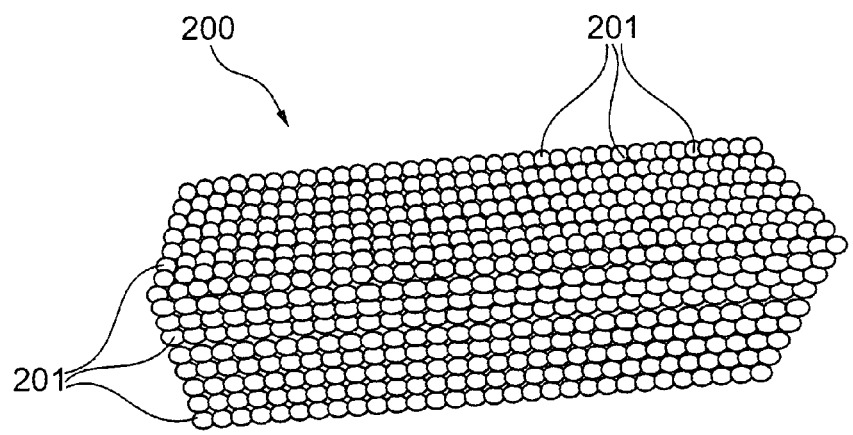
FIG. 2 schematically shows a catalytic converter comprising a catalyst material.

FIG. 2 schematically shows a possible form of a catalytic converter comprising a catalyst material. In general the catalytic converter 200 comprises or substantially consists of a noble metal, e.g. platinum or palladium, and has a great surface to facilitate a reaction, e.g. a release of hydrogen. In particular, the catalytic converter is formed of a plurality of small balls or spheres 201 having a diameter of about 1 mm to 2 mm. These spheres are formed to a structure having a hexagonal, cubic or face-centered cubic arrangement of the spheres. In particular, the arrangement should be as dense as possible to increase the surface the catalyst and the ionic liquid come into contact. The plurality of spheres may be sintered to form the catalytic converter 200. The single spheres 201 may be formed by sintering metal powder, wherein the powder particles have a size in the micrometer or nanometer range, e.g. between 1 nm and 50 micrometer, more particular in the range of 10 nm to 5 micrometer. Due to the fact that the catalytic converter comprises a plurality of balls or spheres the catalytic converter may adopt almost any desired form, e.g. may be cut to the desired form.

Figure 3:
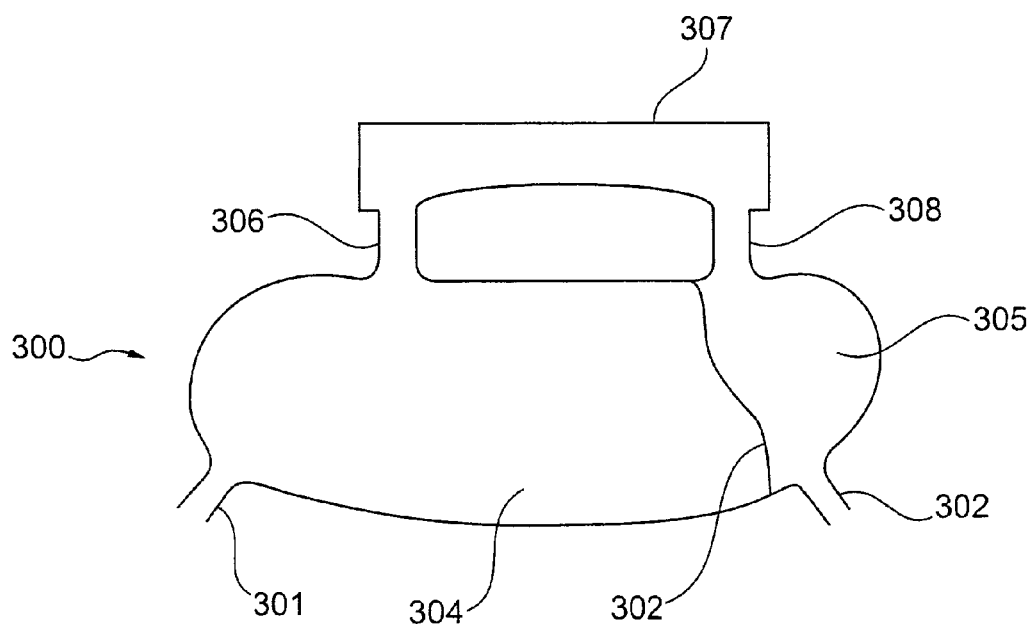
FIG. 3 schematically shows a container for storing a hydrogen storage medium.

FIG. 3 schematically shows a container 300 for storing a hydrogen storage medium. In particular, the container 300 comprises an inlet 301, an outlet 302 and a moveable or flexible membrane 303 separating two chambers or portions of the container from each other. By using the inlet 301 a hydrogen rich ionic liquid, e.g. TOMA-$BH_4$, may be supplied into the container filling the left chamber 304 in FIG. 3, while the outlet 302 may be used to discharge a hydrogen depleted ionic liquid, e.g. TOMA-$BO_2$, from the right chamber 305 in FIG. 3. Furthermore, the container 300 comprises an output connection 306 arranged in the chamber 304 which is connected to an external housing 307 in which a catalytic converter is arranged. That is in the housing the hydrogen is released from the hydrogen rich ionic liquid and the hydrogen depleted ionic liquid is generated. Furthermore, the housing is connected to an input connection 308 of the container 301 which input connection is arranged in the chamber 305.

Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. In a device claim enumerating several means, several of these means may be embodied by one and the same item of software or hardware. The mere fact that certain measures are recited in mutually different dependent claims does not indicate that a combination of these measures cannot be used to advantage.

The invention claimed is:

1. Method of storing hydrogen comprising
forming a first ionic liquid by inducing a borohydride into a second ionic liquid comprising a cation and an anion comprising borate by ion exchange.

2. Method according to claim 1,
wherein the cation is a quaternary or protonated cation.

3. Method according to claim 2,
wherein the cation comprises one to four moieties out of the group consisting of:
hydrogen,
C1-C20-alkyl,
C1-C20-alkenyl,
C1-C20-alkinyl,
C1-C20-cycloalkyl,
C1-C20-cycloalkenyl,
C1-C20-aryl, and
C1-C20-heteroaryl.

4. Method according to claim 3,
wherein the cation is one out of the group consisting of:
pyridinium,
pyrrolium,
thiazolium,
oxazolium, and
quinolinium,
wherein one of the one to four moieties is bound to the nitrogen atom and/or one to three of the one to four moieties are bound to carbon atoms of the carbon ring.

5. Method according to claim 3,
wherein the cation is one out of the group consisting of:
ammonium,
phosphonium, and
sulfonium.

6. Method according to claim 3,
wherein the cation is one out of the group consisting of:
piperidinium,
pyrrolidinium, and
morpholinium,
wherein one or two of the one to four moieties is bound to the nitrogen atom and/or one to three of the one to four moieties are bound to carbon atoms of the carbon ring.

7. Method according to claim 3,
wherein the cation is one out of the group consisting of:
imidazolium,
benzimidazolium,
pyrazolium, and
benzotriazolium,
wherein a respective one of the one to four moieties is bound to each nitrogen atom, and/or one to three of the one to four moieties are bound to carbon atoms of the carbon ring.

8. Method according to claim 2,
wherein the cation is one out of the group consisting of:
trioctylmethylammonium,
tetrahexylammonium,
tetraoctylammonium, and
1-octyl-3-methylimidazolium,
trihexylmethylammonium,
triethylmethylammonium,
tributylmethylammonium,
1-ethyl-3-methylimidazolium,
1,3-dimethylimidazolium,
1-butyl-3-methylimidazolium,
1,2,3-trimethylimidazolium,
1-ethyl-3-methylimidazolium,
1-ethyl-2,3-dimethylimidazolium, and
1-butyl-2,3-dimethylimidazolium.

9. Method of releasing hydrogen comprising:
providing the first ionic liquid according to claim 1, and
forming a second ionic liquid by releasing the hydrogen out of the first ionic liquid by using water and/or a catalyst.

10. Method according to claim 9,
wherein the catalyst forms a microcrystalline or nanocrystalline structure.

11. Method according to claim 1,
wherein the first ionic liquid and/or the second ionic liquid has a predetermined viscosity value.

12. Method according to claim 11,
wherein the viscosity level is set to the predetermined viscosity value by adding an additive.

13. Method according to claim 12,
wherein the additive is one out of the group consisting of:
amide, ether, including cyclic or polyether, acetals, ketals, alcohols, including polyalcohols, aromatic hydrocarbons, aliphatic hydrocarbons, dibutylethers, diethylethers, methyl tert-butyl ethers, ethyl tert-butylethers, 1,2-diethoxyethanes, formaldehyde dimethylacetales, polyethylene glycol dimethylethers, and polyvinyl alcohols.

14. Method according to claim 1, further comprising:
adding a basic additive to the first ionic liquid and/or the second ionic liquid.

15. Method according to claim 14,
wherein the basic additive is at least one out of the group consisting of:
alkaline metal hydroxides,
alkaline earth metal hydroxides,
alkaline metal carbonates,
alkaline earth metal carbonates,
quaternary tetraalkylammonium hydroxides,
quaternary tetraalkylammonium carbonates,
quaternary tetraalkylphosphonium hydroxides,
quaternary tetraalkylphosphonium carbonates, and
quaternary tetraalkylphosphonium alkylcarbonates.

16. The first ionic liquid for storing hydrogen according to claim 1, the first ionic liquid comprising:
a cation, and
borohydride.

17. The second ionic liquid for storing hydrogen according to claim 1, the second ionic liquid comprising:
a cation, and
a borate, in particular metaborate.

18. Method according to claim 9,
wherein the catalyst is a transition metal and/or a noble metal.

* * * * *